United States Patent
Wu et al.

(10) Patent No.: US 12,344,668 B2
(45) Date of Patent: *Jul. 1, 2025

(54) METHODS FOR MODULATING MANNOSE CONTENT OF RECOMBINANT PROTEINS

(71) Applicant: AMGEN INC., Thousand Oaks, CA (US)

(72) Inventors: Jian Wu, Acton, MA (US); Nicole Sabo, Camarillo, CA (US); Michael De La Cruz, Claremont, CA (US); Gregory Flynn, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 1227 days.

This patent is subject to a terminal disclaimer.

(21) Appl. No.: 17/030,842

(22) Filed: Sep. 24, 2020

(65) Prior Publication Data

US 2021/0115125 A1   Apr. 22, 2021

Related U.S. Application Data

(60) Division of application No. 15/150,627, filed on May 10, 2016, now Pat. No. 10,829,551, which is a continuation of application No. 13/741,280, filed on Jan. 14, 2013, now Pat. No. 9,359,435, which is a continuation of application No. 12/569,830, filed on Sep. 29, 2009, now Pat. No. 8,354,105, which is a continuation of application No. 11/644,345, filed on Dec. 22, 2006, now abandoned.

(60) Provisional application No. 60/761,477, filed on Jan. 23, 2006.

(51) Int. Cl.
| | | |
|---|---|---|
| *A61K 39/395* | (2006.01) | |
| *C07K 16/00* | (2006.01) | |
| *C07K 16/24* | (2006.01) | |
| *C12N 5/00* | (2006.01) | |
| *C12P 21/00* | (2006.01) | |
| *A61K 39/00* | (2006.01) | |

(52) U.S. Cl.
CPC ........... *C07K 16/244* (2013.01); *C07K 16/00* (2013.01); *C12N 5/0037* (2013.01); *C12P 21/005* (2013.01); *A61K 2039/505* (2013.01); *C07K 2317/21* (2013.01); *C07K 2317/41* (2013.01); *C07K 2317/56* (2013.01); *C07K 2317/565* (2013.01); *C07K 2317/76* (2013.01); *C12N 2500/02* (2013.01); *C12N 2500/12* (2013.01); *C12N 2500/32* (2013.01); *C12N 2500/34* (2013.01); *C12N 2500/38* (2013.01); *C12N 2500/60* (2013.01); *C12N 2500/74* (2013.01); *C12N 2500/76* (2013.01)

(58) Field of Classification Search
None
See application file for complete search history.

(56) References Cited

U.S. PATENT DOCUMENTS

| | | | |
|---|---|---|---|
| 4,925,796 | A | 5/1990 | Bergh et al. |
| 5,122,469 | A | 6/1992 | Mather |
| 5,232,848 | A | 8/1993 | Wolfe et al. |
| 5,633,162 | A | 5/1997 | Keen |
| 5,721,121 | A | 2/1998 | Etcheverry et al. |
| 6,238,891 | B1 | 5/2001 | Maiorella et al. |
| 6,528,286 | B1 | 3/2003 | Ryall |
| 6,656,466 | B1 | 12/2003 | Etcheverry et al. |
| 7,067,279 | B1 | 6/2006 | Follstad |
| 8,354,105 | B2 | 1/2013 | Wu et al. |
| 2003/0087372 | A1 | 5/2003 | DelaCruz et al. |
| 2003/0138421 | A1 | 7/2003 | van de Winkel et al. |
| 2004/0136986 | A1 | 7/2004 | Raju |
| 2004/0191256 | A1 | 9/2004 | Raju |
| 2005/0069979 | A1 | 3/2005 | Zeng et al. |

FOREIGN PATENT DOCUMENTS

| | | |
|---|---|---|
| EP | 0283942 | 9/1988 |
| EP | 0661060 | 5/2001 |
| WO | 1996-039488 | 12/1996 |
| WO | 2002-000879 | 1/2002 |
| WO | 2003-056914 | 7/2003 |
| WO | 2004-076620 | 9/2004 |
| WO | 2005-011645 | 2/2005 |
| WO | 2005-044303 | 5/2005 |
| WO | 2007-087384 | 1/2007 |

OTHER PUBLICATIONS

Chen et al., "Hyperosmolality leads to an increase in tissue-type plasminogen activator production by a Chinese hamster ovary cell line," Biotechnology Techniques, vol. 12(3), pp. 207-209 (1998).
Kornfeld et al., "Assembly of asparagine-linked oligosaccharides," Ann Rev Biochem., vol. 54, pp. 631-664 (1985).
Rao et al., "5. Conformation of Oligosaccharides," Conformation of Carbohydrates, Hardwood Academic Publishers, pp. 131-141 (1998).
Ryu et al., "Osmoprotective Effect of Glycine Betaine on Foreign Protein Production in Hyperosmotic Recombinant Chinese Hamster Ovary Cell Cultures Differs Among Cell Lines," Biotechnology and Bioengineering, vol. 70(2), pp. 167-175 (2000).
Van Den Steen et al., "Concepts and Principles of O-Linked Glycosylation," Critical Reviews in Biochemistry and Molecular Biology, vol. 33(3), pp. 151-208 (1998).
Andersen et al., "The effect of cell-culture conditions on the oligosaccharide structures of secreted glycoproteins," Current Opinion in Biology, vol. 5, pp. 546-549; 1994.

(Continued)

*Primary Examiner* — Michael D Pak

(74) *Attorney, Agent, or Firm* — Amy C. Madl

(57) ABSTRACT

The present invention relates to methods of modulating (e.g., reducing) the mannose content, particularly high-mannose content of recombinant glycoproteins.

6 Claims, 8 Drawing Sheets

Specification includes a Sequence Listing.

(56) References Cited

OTHER PUBLICATIONS

Bobrowicz et al., "Engineering of an artificial glycosylation pathway blocked in core oligosaccharide assembly in the yeast Pichia pastoris: production of complex humanized glycoproteins with terminal galactose," *Glycobiology*; v: 14 i:9 p. 757-766; Aug. 2004.

Chapman et al., "Putting capillary electrophoresis to work," *Journal LC-GC*, vol. 17, No. 3, pp. 86-99; Feb. 1999.

Davies J, et al: "Expression ofGnTIll in a recombinant anti•CD20 Cho production cell line: Expression of antibodies with altered glycoforms leads to an increase in ADCC through higher affinity for FCy Rill." *Biotechnol Bioeng.*, 74(4):288-94; Aug. 20, 2001.

Goochee, C.F., "Bioprocess factors effecting glycoprotein oligosaccharide structure," *Developments in Biological Standardization*, vol. 76, pp. 95-104; 1992.

Hermeling, et al., "Structure-immunogenicity relationships of therapeutic proteins." *Pharm Res.*; 21(6):897-903; Jun. 2004.

Hu et al., "Large-scale mammalian cell culture." *Curr Opin Biotechnol.* 8:148-53; 1997.

Jenkins et al., Getting the glycosylation right: Implications for the biotechnology industry, *Nature Biotechnology*, Nature Publishing Group, vol. 14, No. 8, pp. 975-981; Aug. 1996.

Kunkel et al, "Comparisons of the glycosylation of a monoclonal antibody produced under nominally identical cell culture conditions in two different bioreactors." *Biotechnol Prog.* 16(3):462.70; May-Jun. 2000.

Li et al., "Optimization of humanized IgGs in glycoengineered Pichia pastoris," *Nature Biotechnology*, vol. 24, No. 2, pp. 210-215; Feb. 2006.

Niwa et al, "IgG subclass-independent improvement of antibody-dependent cellular cytotoxicity by fucose removal from Asn297-linked oligosaccharides." *J Immunol Methods*; 306(1-2):151-60; Nov. 2005.

Olijve et al., Molecular Human Reproduction, 2(5), pp. 371-382; 1996.

Oyaas et al, "Hyperosmotic hybridoma cell cultures: Increased monoclonal antibody production with addition of glycine betaine." *Biotechnol Bioeng.* 44(8):991-8; Oct. 1994.

Petrescu et al., "Statistical analysis of the protein environment of N-glycosylation sites: implications for occupancy, structure, and folding." *Glycobiology* 14(2). 103-114; Sep. 2003.

Product Information, Dulbecco's Modified Eagle's Medium/Ham's Nutrient Mixture F12, Catalog No. 51448C: © SAFC Biosciences, Inc.; Dec. 2006.

Raju, "Glycosylation Variations with Expression Systems and Their Impact on Biological Activity of Therapeutic Immunoglobulins." *BioProcess International.*, 44-52; Apr. 2003.

Rompp Lexikon, 10. Auflage, 416 und 417 (German, and English translation).

Routier, et al., "The glycosylation pattern of a humanized IgGI antibody (D1.3) expressed in CHO cells." *Glycoconjugate Journal.* 14: 201-207; 1997.

Rudd et al., "Rapid, sensitive sequencing of oligosaccharides from glycoproteins," *Current Opinion in Biotechnology*, vol. 8, No. 4, pp. 488-497; 1997.

Ryu et al., "Effect of Hypo-osmotic Stress on Hybridoma Cell Growth and Antibody Production." Biotechnol Bioeng. 55(3):565-70; Aug. 5, 1997.

Schmelzer, "Effects of Elevated Osmolality and Carbon Dioxide on the Glycosylation of Neural Cell Adhesion Molecule and Monoclonal Antibody: Osmoprotectant Compounds as Mitigating Agents," PhD dissertation, Northwestern University, 2001.

Schmelzer, "Hyperosmotic stress and elevated pC02 alter monoclonal antibody charge . . . ," Biotech Progress, 18:2, pp. 346-353; 2002.

Schmelzer., "Effects of osmoprotectant compounds on NCAM polysialylation under . . . ," Biotech and Bioeng, 77:4, pp. 359-368; Feb. 2002.

Sheeley et al., "Characterization of Monoclonal Antibody Glycosylation: Comparison of Expression Systems and Identification of Terminal a-linked Galactose." *Analytical Biochemistry.* 247, 102-110; 1997.

Shields, et al., "Lack of fucose on human IgGI N-linked oligosaccharide improves binding to human FcγRIII and antibody-dependent cellular toxicity." *J Biol. Chem.* 277(30):26733-40; Jul. 2002.

Thomas et al., "Characterization of the glycosylation of a human IgM produced by a human-mouse hybridoma," *Glycobiology*, IRL Press, 5(2) pp. 175-185; 1995.

Waldman, "Targeting the interleukin-15 receptor system in inflammatory autoimmune diseases," *Arthritis Research and Therapy*, v: 6, pp. 174-177; 2004.

Zhu et al., "Production of human monoclonal antibody in eggs of chimeric chickens," *Nature Biotechnology*, vol. 23, No. 9, pp. 1159-1169; Sep. 2005.

METHODS FOR MODULATING MANNOSE CONTENT OF RECOMBINANT PROTEINS

CROSS REFERENCE TO RELATED APPLICATIONS

This application is a divisional application of U.S. application Ser. No. 15/150,627, filed May 10, 2016; which is a continuation application of U.S. application Ser. No. 13/741,280, filed Jan. 14, 2013, now U.S. Pat. No. 9,359,435; which is a continuation application of U.S. application Ser. No. 12/569,830, filed Sep. 29, 2009, now U.S. Pat. No. 8,354,105; which is a continuation application of U.S. application Ser. No. 11/644,345, filed Dec. 22, 2006, now abandoned; which claims the benefit of U.S. Provisional Application No. 60/761,477, filed Jan. 23, 2006, all of which are incorporated by reference herein in their entireties.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 7.57 kilobyte ASCII (Text) file named "A-1059-US-PCD_SeqList.txt"; created on Sep. 24, 2020.

BACKGROUND OF THE INVENTION

Higher eukaryotes perform a variety of post-translational modifications, including methylation, sulfation, phosphorylation, lipid addition and glycosylation. Such modifications may be of critical importance to the function of a protein. Secreted proteins, membrane proteins, and proteins targeted to vesicles or certain intracellular organelles are likely to be glycosylated.

N-linked glycosylation is a form of glycosylation involving addition of oligosaccharides to an asparagine residue found in recognition sequences (e.g., Asn-X-Ser/Thr) in proteins. N-linked glycoproteins contain standard branched structures, which are composed of mannose (Man), galactose, N-acetylglucosamine (GlcNAc) and neuramic acids. Protein N-glycosylation typically originates in the endoplasmic reticulum (ER), where an N-linked oligosaccharide (e.g., $Glc_3$ $Man_9$ $GlcNAc_2$) assembled on dolichol (a lipid carrier intermediate) is transferred to the appropriate Asparagine (Asn) of a nascent protein. This is an event common to all eukaryotic N-linked glycoproteins. There are two major types of N-linked saccharides: high-mannose oligosaccharides, and complex oligosaccharides.

High-mannose oligosaccharides typically include two N-acetylglucosamines with many mannose residues (e.g., greater than 4). Complex oligosaccharides are so named because they can contain almost any number of the other types of saccharides, including more than the original two N-acetylglucosamines. Proteins can be glycosylated by both types of oligosaccharides on different portions of the protein. Whether an oligosaccharide is high-mannose or complex is thought to depend on its accessibility to saccharide-modifying proteins in the Golgi apparatus. If the saccharide is relatively inaccessible, it will most likely stay in its original high-mannose form. If it is accessible, then it is likely that many of the mannose residues will be cleaved off and the saccharide will be further modified by the addition of other types of group as discussed above.

After an oligosaccharide chain has been added to a protein, the three glucose and one mannose residues are removed by three different enzymes in a fixed order. This event occurs in the ER and is a signal that the protein can be transported to the Golgi for further processing. After the processing in the ER, the high-mannose type oligosaccharide is formed. The three glucose residues and one specific alpha-1,2-linked mannose residue are removed by specific glucosidases and an alpha-1,2-mannosidase in the ER, resulting in the core oligosaccharide structure, $Man_8$ $GlcNAc_2$. The protein with this core sugar structure is transported to the Golgi apparatus where the sugar moiety undergoes various modifications.

In mammalian cells, the modification of the sugar chain proceeds via 3 different pathways depending on the protein moiety to which it is added. The three different pathways are: (1) the core sugar chain does not change; (2) the core sugar chain is changed by adding the N-acetylglucosamine-1-phosphate moiety (GlcNAc-1-P) in UDP-N-acetyl glucosamine (UDP-GlcNAc) to the 6-position of mannose in the core sugar chain, followed by removing the GlcNAc moiety to form an acidic sugar chain in the glycoprotein; or (3) the core sugar chain is first converted into $Man_5$ $GlcNAc_2$ by removing 3 mannose residues with mannosidase 1; $Man_5$ $GlcNAc_2$ is further modified by adding GlcNAc and removing 2 more mannose residues, followed by sequentially adding GlcNAc, galactose (Gal), and N-acetylneuraminic acid (also called sialic acid (NeuNAc)) to form various hybrid or complex sugar chains (R. Kornfeld and S. Kornfeld, Ann. Rev. Biochem. 54: 631-664 (1985); Chiba et al., J. Biol. Chem. 273: 26298-26304 (1998)).

The oligosaccharide content of recombinant proteins can affect the safety and efficacy of therapeutic glycoproteins. Accordingly, methods for controlling the oligosaccharide content, particularly the mannose content, of such glycoproteins would be beneficial.

The high mannose content of glycoprotein compositions, particularly therapeutic antibodies, can significantly affect the safety and efficacy of such proteins during therapeutic use. Without being bound by a particular theory, evidence suggests that high-mannose glycoproteins are cleared from circulation faster than their low mannose counterparts due to, for example, mannose receptors on macrophages and dendritic cells. Additionally, high mannose glycoproteins are expected to be more immunogenic. Accordingly, it is desirable to produce therapeutic glycoproteins such as, for example, therapeutic antibodies, having low mannose content.

The present inventors solves this need in the art by providing methods for modulating (e.g., controlling or reducing) the mannose content of recombinantly produced proteins and peptides.

SUMMARY OF THE INVENTION

The present invention is based, at least in part, on the discovery of factors that affect mannose content and, in particular, high-mannose content, of recombinantly expressed glycoproteins.

Accordingly, in one aspect, the present invention provides a method of modulating the mannose content (i.e., on an oligosaccharide side chain) of a recombinant glycoprotein produced in a mammalian host cell by manipulating the cell culture conditions such that the glycoprotein produced by the cell has low-mannose content. As used herein, the term "low-mannose content" refers to glycoprotein compositions wherein less than about 10%, or less than about 8%, or less than about 5% (e.g., about 4% or less) of the glycoproteins in the composition have more than 4 mannose residues (i.e., are species of M5 or greater). As used herein, the term "low-mannose content" also refers to glycoprotein compositions wherein less than about 10%, less than about 9%, less than about 8%, less than about 7%, less than about 6%, less than about 5%, less than about 4%, less than about 3%, less than about 2%, less than about 1%, or any values between any of these preceding ranges, or even at zero.

In one embodiment of the invention, low-mannose content is achieved by maintaining the cell culture environment at low osmolality (e.g., less than about 600 mOsm/Kg, or less than about 500 mOsm/Kg, or less than about 400 mOsm/Kg, e.g., between about 380 to 250 mOsm/Kg). This enriches the cell culture for glycoproteins having low mannose-content i.e., having 4 or fewer mannose residues on the oligosaccharide side chains of the glycoprotein. Accordingly, in a particular embodiment, the invention provides a method for producing a recombinant glycoprotein having low-mannose content comprising culturing a mammalian host-cell (e.g., in an expansion or production phase of the culture) which expresses the glycoprotein in a medium having an osmolality of about 600 mOsm/Kg or less (e.g., between a range of about 200 and 600 mOsm/Kg, e.g., about 250 and 350 mOsm/Kg, about 250 and 500 mOsm/Kg, about 250 and 450 mOsm/Kg, about 250 and 400 mOsm/Kg, about 250 and 380 mOsm/Kg, or about 250 and 350 mOsm/Kg).

The foregoing osmolality ranges can be achieved by manipulating a number of cell culture parameters including, but not limited to, concentrations of one or more of salts, vitamins, sugars, peptones and amino acids in the cell culture medium. Accordingly, in a particular embodiment, the invention provides a method of producing a recombinant glycoprotein having low-mannose content by culturing a host-cell which expresses the glycoprotein in a medium containing potassium at a concentration of about 70 mM or less (e.g., about 10 mM to about 50 mM); and/or sodium at a concentration of about 200 mM or less (e.g., about 50 mM to about 100 mM) and maintaining the osmolality of the cell culture at about 600 mOsm/Kg or less.

In still another embodiment, the invention provides a method of producing a recombinant glycoprotein having low-mannose content by culturing a host-cell which expresses the glycoprotein in a medium which is substantially free of one or more amino acids selected from the group consisting of alanine, arginine, aspartic acid and glutamic acid, and maintaining the osmolality of the cell culture at about 600 mOsm/Kg or less.

In addition, in still another embodiment, the medium can include one or more vitamins selected from the group consisting of biotin, D-calcium pantothenate, choline chloride, folic acid, i-inositol, niacinamide, pyridoxal HCl, pyridoxine HCl, riboflavin, thiamine HCl and cyanocobalamin, at a concentration of about 0.00005 g/L to about 0.9 g/L. In yet another embodiment, the medium includes glucose at a concentration of about 1 mM to about 90 mM. In a further embodiment, the medium includes one or more peptones selected from the group consisting of yeast extract, yeast hydrolysate, soy peptone, soy hydrolysate, wheat peptone and wheat hydrolysate, at a concentration of about 0.5 g/L to about 60 g/L.

In yet a further embodiment of the present invention, the cell culture medium can include one or more osmoprotectants in an amount necessary to maintain the osmolality at a desired level, e.g., about 600 mOsm/Kg or less. Suitable osmoprotectants are known in the art and include, for example, betaine, glycine, L-threonine and L-proline, and derivatives thereof such as, for example, glycine betaine and betaine aldehyde. In a particular embodiment, the osmoprotectant (e.g., betaine) is present at a concentration of about 20 mM or greater in the cell culture medium. In particular embodiments, the osmoprotectant (e.g., betaine) is present at a concentration of about 1 mM to about 100 mM or at about 20 mM to about 30 mM.

Additional cell culture parameters that may be controlled, either alone or in combination with one or more of the parameters described herein include, for example, temperature and duration of time which the cells are cultured for. In certain embodiments, a host-cell expressing a recombinant glycoprotein is cultured at a temperature of about 31° C. to about 38° C. In certain other embodiments, a host cell expressing a recombinant glycoprotein is cultured for a period ranging from about 5 days to about 14 days.

Suitable host cells for expressing recombinant glycoproteins according to the present invention are well known in the art and include any of those described herein, such as CHO cells, lymphocytic cells (e.g., NSO cells) and a variety of other mammalian cells.

The present invention can be employed to product a wide variety of glycoproteins having low-mannose content as described herein. In a particular embodiment, the invention is used to produce a recombinant monoclonal antibody or an antigen-binding fragment thereof having low-mannose content. Suitable antibodies can include, for example, murine, chimeric, humanized and fully human antibodies, as well as other antibody forms known in the art. In another particular embodiment, the antibody binds IL-15, which includes but are not limited to the antibodies disclosed in U.S. Publication No.: 2003-0138421, which is incorporated by reference herein in its entirety. In another particular embodiment, the antibody is a fully human monoclonal antibody that binds IL-15 having a light chain variable region comprising the amino acid sequence set forth in SEQ ID NO:4 and/or a heavy chain variable region comprising the amino acid sequence set forth in SEQ ID NO:2, as well as homologous sequences which bind IL-15 (e.g., having amino acid sequences of about 80, 85, 90, 95% or greater identity to SEQ ID NO: 4 or SEQ ID NO: 2, respectively). In a further particular embodiment, the antibody is a human antibody that binds IL-15, or an antigen-binding fragment thereof, having a light chain variable region comprising one or more complementarity determining regions (CDRs) set forth in SEQ ID NOs:8-10, as well as homologous sequences which bind IL-15 (e.g., having amino acid sequences of about 80, 85, 90, 95% or greater identity to any of SEQ ID NOS: 8-10, respectively), and a heavy chain variable region comprising one or more complementarity determining regions (CDRs) set forth in SEQ ID NOs:5-7 as well as homologous sequences which bind IL-15 (e.g., having amino acid sequences of about 80, 85, 90, 95% or greater identity to any of SEQ ID NOS: 5-7, respectively). In a particular embodiment, a human monoclonal antibody that binds IL-15 or an antigen-binding fragment thereof, includes a light chain variable region comprising all three CDRs set forth in SEQ ID NOs:8-10, and a heavy chain variable region comprising all three CDRs set forth in SEQ ID NOs: 5-7, or conservative amino acid substitutions thereof.

In yet another aspect, the present invention provides recombinant glycoproteins having low-mannose content produced by the methods described herein. Accordingly, such glycoproteins may include any of the aforementioned therapeutic glycoproteins, such as antibodies, hormones, enzymes, peptides and other glycoproteins.

Also encompassed by the present invention are compositions comprising any of the aforementioned glycoproteins having low-mannose content. In a particular embodiment, the composition is a pharmaceutical composition that includes an isolated glycoprotein (e.g., an isolated human monoclonal antibody that binds IL-15 or an antigen binding fragment thereof) having low-mannose content and a pharmaceutically acceptable carrier.

Accordingly, in still another aspect, the present invention provides a method of treating or preventing a disorder that is associated with an overexpression of human IL-15 and/or in which a downregulation or inhibition of human IL-15 induced effects is beneficial is provided, by administering to a subject an isolated IL-15 antibody having low-mannose content. Exemplary disorders include, but are not limited to, vasculitis, psoriasis, multiple sclerosis, rheumatoid arthritis, inflammatory bowel disease (e.g., Crohn's disease or celiac disease), allograft rejection, graft versus host disease, T-cell lymphoma, and T-cell leukemia.

Accordingly, in still another aspect, the present invention provides a method of treating or preventing a disorder that is associated with an overexpression of human IL-15 and/or in which a downregulation or inhibition of human IL-15 induced effects is beneficial is provided, by administering to a subject an isolated IL-15 antibody having low-mannose content. Exemplary disorders include, but are not limited to, athritides, connective tissue disorders, ophthalmological disorders, neurological disorders, gastrointestinal and hepatic disorders, allergic disorders, hematologic disorders, skin disorders, pulmonary disorders, malignancies, transplantation-derived disorders, endocrinologic disorders, vascular disorders, gynecological disorders and infectious diseases.

DETAILED DESCRIPTION OF THE INVENTION

Figure 1:
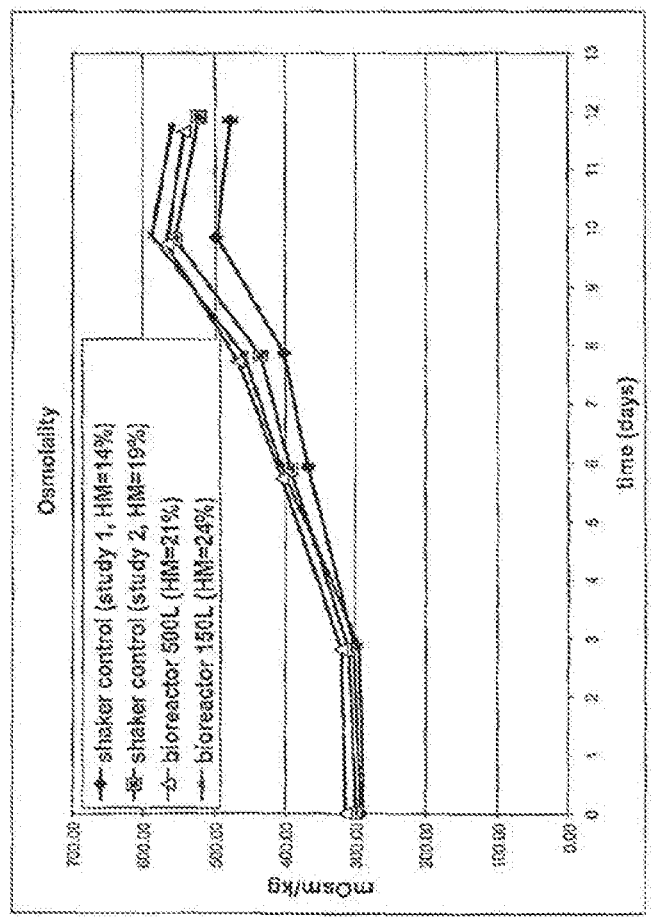
FIG. 1 is a graph depicting the correlation between osmolality and high-mannose content of a fully human monoclonal antibody that binds IL-15 produced by culturing cells expressing the antibody in shaker control (50 mL) and bioreactors (150 L and 500 L).

Accordingly, it is desirable to produce therapeutic glycoproteins such as, for example, therapeutic antibodies, having low-mannose content.

In order that the present disclosure may be more readily understood, certain terms are first defined. Additional definitions are set forth throughout the detailed description.

I. Definitions

Carbohydrate moieties are described herein with reference to commonly used nomenclature for oligosaccharides. A review of carbohydrate chemistry which uses this nomenclature can be found, for example, in Hubbard and Ivatt, Ann. Rev. Biochem. 50:555-583 (1981). This nomenclature includes, for instance, Man, which represents mannose; GlcNAc, which represents 2-N-acetylglucosamine; Gal which represents galactose; and Glc, which represents glucose. Sialic acids are described with reference to the shorthand notation NeuNAc, for 5-N-acetylneuraminic acid, and NeuNGc for 5-glycolylneuraminic acid.

The term "osmolality," as used herein, refers to a measure of the osmotic pressure of dissolved solute particles in an aqueous solution. The solute particles include both ions and non-ionized molecules. Osmolality is expressed as the concentration of osmotically active particles (i.e., osmoles) dissolved in 1 kg of solution (1 mOsm/kg $H_2O$ at 38° C. is equivalent to an osmotic pressure of 19 mm Hg). As used herein, the abbreviation "mOsm" means "milliosmoles/kg solution," In exemplary embodiments, osmolality of the cell culture medium is maintained at about 600 mOsm/Kg or less, or at about 550 mOsm/Kg or less, or at about 500 mOsm/Kg or less, or at about 450 mOsm/Kg or less, or at about 400 mOsm/Kg or less, or at about 380 mOsm/Kg or less, or between at about 200 mOsm/Kg and about 600 mOsm/Kg, or between at about 250 mOsm/Kg and about 550 mOsm/Kg, or between at about 250 mOsm/Kg and about 500 mOsm/Kg, or between at about 250 mOsm/Kg and about 450 mOsm/Kg, or between at about 250 mOsm/Kg and about 400 mOsm/Kg, or between at about 250 mOsm/Kg and about 380 mOsm/Kg, or between at about 250 mOsm/Kg and about 350 mOsm/Kg.

As used herein, the term "glycoprotein" refers to peptides and proteins, including antibodies, having at least one oligosaccharide side chain including mannose residues. Glycoproteins may be homologous to the host cell, or may be heterologous, i.e., foreign, to the host cell being utilized, such as, for example, a human glycoprotein produced by a Chinese hamster ovary (CHO) host-cell. Such glycoproteins are generally referred to as "recombinant glycoproteins." In certain embodiments, glycoproteins expressed by a host-cell are directly secreted into the medium. Examples of mammalian glycoproteins include the following molecules and antibodies against thereto, cytokines, e.g., IL-1 to IL-15, and their receptors; chemokines, such as TNF, TECK, and their receptors, e.g., TNFRs, CCR9; growth hormone, including human growth hormone, and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; plasminogen activator, such as urokinase or human urine or tissue-type plasminogen activator (t-PA); bombesin; thrombin; hemopoietic growth factor; enkephalinase; RANTES (regulated on activation normally T-cell expressed and secreted); human macrophage inflammatory protein (MIP-1-alpha); serum albumin such as human serum albumin; mullerian-inhibiting substance; relaxin A-chain;

relaxin B-chain; prorelaxin; mouse gonadotropin-associated peptide; a microbial protein, such as beta-lactamase; DNase; inhibin; activin; vascular endothelial growth factor (VEOF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NG-beta; platelet-derived growth factor (PDGF); fibroblast growth factor such as aFGF and bFGF; epidermal growth factor (EGF); transforming growth factor (TGF) such as TGF-alpha and TGF-beta, including TGF-beta1, TGF-beta2, TGF-beta3, TGF-beta4, or TGF-beta5; insulin-like growth factor-I and -II (IGF-I and IGF-II); des(1-3)-IGF-I (brain 1GF-1), insulin-like growth factor binding proteins; CD proteins such as CD-3, CD-4, CD-8, and CD-19; erythropoietin; osteoinductive factors; immunotoxins; bone morphogenetic protein (BMP); interferons such as interferon-alpha, -beta, and -gamma; colony stimulating factors (CSFs), e.g., M-CSF, GM-CSF, and G-CSF; interleukins (ILs), e.g., TL-1 to IL-15; superoxide dismutase; T-cell receptors; surface membrane proteins; decay accelerating factor; viral antigen such as, for example, a portion of the AIDS envelope; transport proteins; homing receptors; and regulatory proteins.

As used herein, the terms "cell culture medium" and "culture medium" refer to a nutrient solution used for growing mammalian cells that typically provides at least one component from one or more of the following categories: 1) an energy source, usually in the form of a carbohydrate such as, for example, glucose; 2) one or more of all essential amino acids, and usually the basic set of twenty amino acids plus cysteine; 3) vitamins and/or other organic compounds required at low concentrations; 4) free fatty acids; and 5) trace elements, where trace elements are defined as inorganic compounds or naturally occurring elements that are typically required at very low concentrations, usually in the micromolar range. The nutrient solution may optionally be supplemented with additional components to optimize growth of cells.

The mammalian cell culture of the present invention is prepared in a medium suitable for the particular cell being cultured. Suitable cell culture media that may be used for culturing a particular cell type would be apparent to one of ordinary skill in the art. Exemplary commercially available media include, for example, Ham's F10 (SIGMA). Minimal Essential Medium (MEM, SIGMA), RPMI-1640 (SIGMA), and Dulbecco's Modified Eagle's Medium (DMEM, SIGMA). Any of these or other suitable media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™), trace elements (defined as inorganic compounds usually present at final concentrations in the micromolar range) lipids (such as linoleic or other fatty acids) and their suitable carriers, and glucose or an equivalent energy source, and/or modified as described herein to facilitate production of recombinant glycoproteins having low-mannose content. In a particular embodiment, the cell culture medium is serum-free.

In certain embodiments, a cell culture medium is optimized so as to modulate (e.g., reduce) the high-mannose content of a recombinant glycoprotein expressed by a host-cell cultured in such medium. In a particular embodiment, the mammalian host cell is a CHO cell and a suitable medium contains a basal medium component such as a DMEM/HAM F-12 based formulation with modified concentrations of one or more components such as, for example, amino acids, salts, sugars, peptones and vitamins, so as to modulate (e.g., reduce) the high-mannose content of a recombinant glycoprotein expressed by a CHO cell cultured in such medium.

The term "growth phase" of a cell culture refers to the period of exponential cell growth (i.e., the log phase) where the cells are generally rapidly dividing. Cells are maintained at the growth phase for a period of about one day, or about two days, or about three days, or about four days, or longer than four days. The duration of time for which the cells are maintained at growth phase will vary based on the cell-type and rate of growth of cells and the culture conditions, for example.

The term "transition phase" refers to a period of time between the growth phase and the production phase. Generally, transition phase is the time during which culture conditions may be controlled to support a shift from growth phase to production phase. Various cell culture parameters which may be controlled include but are not limited to, one or more of, temperature, osmolality, vitamins, amino acids, sugars, peptones, ammonium and salts.

The term "production phase" of a cell culture refers to the period of time where the cell growth has plateaued. The logarithmic cell growth typically ends before or during this phase and protein production takes over. It is desirable to supplement the cell culture medium so as to achieve the desired protein production at this stage.

The terms "mammalian host cell," "host-cell," and "mammalian cell" refer to cell lines derived from mammals that are capable of growth and survival when placed in either monolayer culture or in suspension culture in a medium containing the appropriate nutrients and growth factors. Typically, such cells are capable of expressing and secreting large quantities of a particular glycoprotein of interest into the culture medium. Examples of suitable mammalian host cells include, but are not limited to, Chinese hamster ovary cells/–DHFR (Urlaub and Chasin, Proc. Natl. Acad. Sci. USA, 77:4216 (1980)); dp12CHO cells (EP 307247); monkey kidney CV1 line transformed by SV40 (ATCC CRL 1651); human embryonic kidney line (293 or 293 cells subcloned for growth in suspension culture) (Graham et al., J. Gen Virol., 36:59 (1977)); baby hamster kidney cells (ATCC CCL 10); mouse sertoli cells (TM4) (Mather, Bibl. Reprod., 23:243-251 (1980)); monkey kidney cells (ATCC CCL 70); African green monkey kidney cells (VERO-76) (ATCC CRL-1587); human cervical carcinoma cells (HeLa) (ATCC CCL 2); canine kidney cells (MDCK) (ATCC CCL 34); buffalo rat liver cells (BRL 3A) (ATCC CRL 1442); human lung cells (W138)(ATCC CCL 75); human liver cells (Hep 02 HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2).

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "expression," "express" and "expresses" generally refer to transcription and translation occurring within a host-cell. The level of expression of gene product in a host cell may be determined on the basis of either the amount of corresponding mRNA that is present in the cell or the amount of the protein encoded by the gene. For example, mRNA transcribed from a product gene can be quantitated by northern hybridization. (Sambrook et al., Molecular Cloning: A Laboratory Manual, pp. 7.3-7.57, Cold Spring Harbor Laboratory Press (1989)). A protein encoded by a gene can be quantitated either by assaying for the biological activity of the protein or by employing assays that are independent of such activity, such as, for example, western blotting analysis or radioimmunoassay using antibodies that are capable of reacting with the protein. (Sambrook et al., Molecular Cloning: A Laboratory Manual, pp. 18.1-18.88 Cold Spring Harbor Laboratory Press (1989)). In some embodiments, the terms "expression," "express" and "expresses" are used in reference to a recombinant protein having low-mannose content produced by a method of the invention.

The terms "low-mannose" and "low-mannose content," as used herein, refer to a glycoprotein composition, where no more than about 10% of the composition comprises glycoproteins having more than 4 mannose residues, i.e., species M5 or greater. Conversely, "high-mannose content" refers to a glycoprotein composition where more than about 10% of the composition comprises glycoproteins having more than 4 mannose residues. The terms "low mannose" and "low mannose content," are also used in reference to a glycoprotein composition including greater than about 90%, or greater than about 95% of the composition having glycoproteins including 4 or fewer than 4 mannose residues.

The term "a glycoprotein having low-mannose content" is used in reference to a recombinant glycoprotein composition, which when produced by culturing a host-cell, includes, but are not limited thereto, no more than about 4%, no more than about 5%, no more than between about 4% and about 5%, no more than about 6%, no more than between about 5% and 6%, no more than about 7%, no more than between about 6% and 7%, no more than about 8%, no more than about 7% and 8%, no more than about 9%, no more than between 8% and 9%, no more than about 10%, or no more than between about 9% and 10% of the glycoproteins in the composition having greater than 4 mannose residues (i.e., species M5 or greater). Accordingly, the term "a glycoprotein having low-mannose content" refers to a recombinant glycoprotein composition, which when produced by culturing a host-cell, includes greater than about 90%, or greater than about 95%, of the glycoproteins in the composition having 4 or fewer than 4 mannose residues (i.e., 0-4 mannose residues).

The high-mannose content can be measured by one or more methods well-known in the art, for instance, as described in Wuhrer et al. (Journal of Chromatography B Vol. 825:124-133, 2005) and Dell et al. (Science Vol. 291:2351-2356), and those described herein including, for example, the analytical method for N-Glycan mapping of glycoproteins Briefly, N-glycans are removed enzymatically from the recombinant glycoproteins, such as a recombinant monoclonal antibody, and labeled with a fluorescent tag (2-Aminobenzamide) at the reducing terminus. The fluorescent N-glycans are separated by high pH anion exchange chromatography (HPAEC), and detected using fluorescence detection. Separation of the neutral N-glycans is generally based on the increasing complexity in the N-glycan structures. Separation of the charged N-glycans is based on the number and type of sialic acid, sulfate, or other modifications present from which a charge number can be derived. These glycan profiles of test samples are compared visually to an appropriate standard.

The high-mannose content can also be measured using a method instantly disclosed herein: a high-throughput method for detecting and/or quantitating the high-mannose content of a glycoprotein, including but not limited to, antibody or fragments thereof, e.g., Fab fragments, fusion proteins comprising Fc fragments and peptibody when expressed in eukaryotic host cells. Antibodies typically have a single N-linked glycan on the Fc region. Because of the partially buried structure of the glycan, it is often only partially processed, resulting in excess high mannose and hybrid types. Clone selection, mutation of cells or other genetic manipulation, or cell culture manipulation can alter the types of glycans produced by the cells. Large numbers of conditions/cells are explored thus many glycan tests are required during screening. Traditional glycan mapping is slow and labor intensive, requiring multiple days. The high-mannose/hybrid glycan assay of the present invention provides ratios of glycan types much faster with much less operator effort.

In particular, the invention provides a method for detecting and/or quantitating the high-mannose content of a glycoprotein in a sample or a composition comprising said glycoprotein, said method comprises subjecting the sample or the composition comprising the glycoprotein to an endoglycosidase digestion, reducing the digested glycoproteins using a reducing agent (if required), and separating the digested glycoproteins by denature electrophoresis whereby the ratio of high-mannose/hybrid type glycan is determined by subtracting the fraction of non-glycosylated heavy chain (peak fraction without endoglycosidase treatment) from the fraction of de-glycosylated heavy chain (peak following endoglycosidase digestion). The non-glycosylated heavy chain fraction or the peak fraction without endoglycosidase treatment is generated by subjecting the same sample or composition to the same digestion condition except that no endoglycosidase is present therein. This step can be carried out concurrently with or separately from the endoglycosidase digestion step.

Any endoglycosidases that selectively cleave high mannose and hybrid glycans between GlcNAc1 and GlcNAc2 on the core glycan (or generating short glycans on the protein), while leaving complex N-linked glycans intact can be used in this invention. For proper quantitation, endoglycosidase must not be in limiting quantities. The specific condition for carrying out the endoglycosidase digestion, including the concentration of the enzyme, the incubation temperature and digestion time, depends on the type of endoglycosidase used. Examples of endoglycosidases related to this invention include but are not limited to Endoglycosidase H and Endoglycosidase FL In one embodiment of the present invention, the sample comprising the glycoproteins is treated with Endogycosidase H at 37° C. for about 2 hours, reduced with β-mercaptoethanol, and subjected to CE-SDS analysis.

Example methods for separating the de-glycosylated glycoproteins, e.g., do-glycosylated antibody, from the glycosylated glycoproteins, e.g., glycosylated antibody, include but are not limited to the following two methods:

1) CE-SDS under reducing conditions. The glycosylated glycoprotein, e.g., an antibody, is denatured with SDS and a reducing agent and the heavy chain (HC) thereof with the glycan is separated from the cleaved HC (de-glycosylated HC) by Capillary Electrophoresis-SDS (CE-SDS). An electropherogram is generated of the UV signal. The areas under the peaks are proportional to the relative amounts. Therefore the amount of High-mannose/hybrid type is determined from the fraction eluting at the earlier de-glycosylated HC position. Since the GlcNAc-HC co-migrates with de-glycosylated HC, the % de-glycosylated HC from an undigested sample is subtracted from pro-peak of a digested sample to yield the % high mannose value. Separation requires 15-30 minutes, depending on the configuration.

2) Microfluidic-based CE-SDS. The glycoprotein is denatured as in 1) but separated using a "lab on a chip" instrument, such as the LC90 by Caliper. The same principle is used in the assay and the separation, though a fluorescent dye is used to detect the protein. Separation time is reduced to about 30 seconds per assay and it can be sampled from a microtiter plate.

The method of the present invention as described above can be performed on purified protein but also on crude cell culture samples. With recombinant antibodies, the signal is strong enough that purification is not required.

In certain embodiments, glycoproteins having more than 4 mannose residues include glycoproteins having 5 to 9 mannose residues (i.e., species M5-M9). Without wishing to be bound by a particular theory, one of ordinary skill in the art will understand that a glycoprotein composition expressed by a host-cell includes glycoproteins with varying number of mannose residues. For example, the low-mannose glycoproteins have 4 or fewer than 4 mannose residues (e.g., 0-4 mannose residues), and the high-mannose glycoproteins have greater than 4 mannose residues (e.g., M5 species or higher).

In a particular embodiment of the invention, a glycoprotein having low-mannose content is a recombinant antibody or an antigen-binding fragment thereof. In another particular embodiment of the invention, a recombinant glycoprotein having low-mannose content is a human monoclonal antibody that binds IL-15 or an antigen-binding fragment thereof.

The term "substantially free," as used herein, generally refers to preparations of a cell culture medium which is free or has a reduced amount (i.e., relative to unmodified culture medium) of certain components. For example, in one embodiment, the culture medium used for producing recombinant glycoproteins having low mannose content is substantially free of certain amino acids (e.g., one or more amino acids selected from the group consisting of alanine, arginine, aspartic acid and glutamic acid). In some embodiments, a culture medium substantially free of one or more components is modified to include less than about 1%, or less than about 3%, or less than about 5%, or less than about 10% of one or more such components relative to the unmodified culture medium.

The terms "IL-15," "IL-15 antigen" and interleukin 15" are used interchangeably herein, and include any variants or isoforms which are naturally expressed by cells.

The term "antibody" as referred to herein includes whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The terms "antigen-binding portion" and "antigen-binding fragment" of an antibody (or simply "antibody portion"), as used herein, refer to one or more fragments of an antibody that selectively bind to an antigen (e.g., IL-15). It has been shown that the antigen-binding function of an antibody can be performed by fragments of a full-length antibody. Examples of antigen-binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., Nature 341:544-546 (1989)), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. Science 242:423-426 (1988); and Huston et al. Proc. Natl. Acad. Sci. USA 85:5879-5883 (1988). Such single chain antibodies are also intended to be encompassed within the terms "antigen-binding portion" and "antigen-binding fragment" of an antibody. These antibody fragments are obtained using conventional techniques known to those with skill in the art, and the fragments are screened for utility in the same manner as are intact antibodies.

The term "monoclonal antibody" as used herein, refers to an antibody which displays a single binding specificity and affinity for a particular epitope. Accordingly, the term "human monoclonal antibody" refers to an antibody which displays a single binding specificity and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

An "isolated antibody," as used herein, refers to an antibody which is substantially free of other antibodies having different antigenic specificities (e.g., an isolated antibody that specifically binds to IL-1 Sis substantially free of antibodies that specifically bind antigens other than IL-15). An isolated antibody that specifically binds to an epitope of IL-15 may, however, have cross-reactivity to other related cytokines or to other IL-15 proteins from different species. However, the antibody preferably always binds to human IL-15. In addition, an isolated antibody is typically substantially free of other cellular material and/or chemicals. In a particular embodiment, a combination of "isolated" monoclonal antibodies having different IL-15 specificities are combined in a well defined composition.

As used herein, "specific binding," "selective binding" and "selectively binds," refer to an antibody or a fragment thereof, binding to a predetermined antigen. For example, in one embodiment, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument using recombinant human IL-15 as the analyte and the antibody as the ligand, and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which selectively binds to an antigen."

The term "$K_D$," as used herein, is intended to refer to the dissociation equilibrium constant of a particular antibody-antigen interaction.

As used herein, "isotype" refers to the antibody class (e.g., IgM or IgG) that is encoded by heavy chain constant region genes.

As used herein, "isotype switching" refers to the phenomenon by which the class, or isotype, of an antibody changes from one Ig class to one of the other Ig classes.

As used herein, "non-switched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human a, and human $\Sigma_\mu$ ($\delta$-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a µ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the non-human transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "nucleic acid molecule," as used herein, refers to DNA and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., $V_H$, $V_L$, CDR3) that selectively bind to L-15, refer to a nucleic acid molecule in which the nucleotide sequences encoding the antibody or antibody portion are free of other nucleotide sequences-encoding antibodies or antibody portions that bind antigens other than IL-15, which other sequences may naturally flank the nucleic acid in human genomic DNA. SEQ ID NOS: 1-4 correspond to the nucleotide and amino acid sequences comprising the heavy chain ($V_H$) and light chain ($V_L$) variable regions of a human anti-IL-15 antibody. In particular, SEQ ID NO:1 and 2 correspond to the $V_H$ of the antibody and SEQ ID NO:3 and 4 correspond to the $V_L$ of the antibody.

In a particular embodiment, a human monoclonal antibody that binds IL-15, or an antigen binding fragment thereof, includes a light chain variable region comprising one or more and preferably all three CDRs set forth in SEQ ID NOs:8-10 and a heavy chain variable region comprising one or more and preferably all three CDRs set forth in SEQ ID NOs:5-7.

In a particular embodiment, the present invention also encompasses "conservative sequence modifications" or "conservative sequence substitutions" of the sequences set forth in SEQ ID NOs:1-10, i.e., nucleotide and amino acid sequence modifications which do not significantly affect or alter the binding characteristics of the antibody encoded by the nucleotide sequence or containing the amino acid sequence. Such conservative sequence modifications include nucleotide and amino acid substitutions, additions and deletions. Modifications can be introduced into SEQ ID NOs:1-10 by standard techniques known in the at, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a human anti-IL-15 antibody is preferably replaced with another amino acid residue from the same side chain family.

Alternatively, in another embodiment, mutations can be introduced randomly along all or part of an anti-IL-15 antibody coding sequence, such as by saturation mutagenesis, and the resulting modified anti-IL-15 antibodies can be screened for binding activity.

Accordingly, antibodies encoded by the (heavy and light chain variable region) nucleotide sequences disclosed herein and/or containing the (heavy and light chain variable region) amino acid sequences disclosed herein (i.e., SEQ ID NOs: 1-4) include substantially similar antibodies encoded by or containing similar sequences which have been conservatively modified. Further, discussion as to how such substantially similar antibodies can be generated based on the partial (i.e., heavy and light chain variable regions) sequences disclosed herein as SEQ ID Nos:1-4 is provided below.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For amino acid sequences, the term "homology" indicates the degree of identity between two amino acid sequences when optimally aligned and compared with appropriate insertions or deletions.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et at J. Mol. Biol 215:403-10 (1990). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., Nucleic Acids Res, 25(17):3389-3402 (1997). When utilizing BLAST and Gapped BLAST programs, the default parameters of the respective programs (e.g., XBLAST and NBLAST) can be used. (See http://www.ncbi.nm.nih.gov).

The nucleic acids may be present in whole cells, in a cell lysate, or in a partially purified or substantially pure form. A nucleic acid is "isolated" or "substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the an. See, F. Ausubel, et al., ed. Current Protocols in Molecular Biology, Greene Publishing and Wiley Interscience, New York (1987).

Nucleic acid compositions of the present invention, while often in a native sequence (except for modified restriction sites and the like), from either cDNA, genomic or mixtures thereof, may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the present invention is intended to include such other forms of expression vectors, such as viral vectors (e.g., replication defective retroviruses, adenoviruses and adeno-associated viruses), which serve equivalent functions.

As used herein, the term "subject" includes any human or non-human animal. For example, the methods and compositions of the present invention can be used to treat a subject having an inflammatory disease, such as arthritis, e.g., rheumatoid arthritis. The term "non-human animal" includes all vertebrates, e.g., mammals and non-mammals, such as non-human primates, sheep, dog, cow, chickens, amphibians, reptiles, etc.

Various aspects of the invention are described in further detail in the following subsections.

II. Factors Effecting Mannose Content (a) Osmolality

Various cell culture parameters can affect the mannose content of a recombinant glycoprotein expressed in mammalian cell culture. In particular, it was discovered by way of the present invention that the higher the osmolality of the cell culture medium is, the higher the percentage of glycoproteins in the composition having more than 4 mannose residues (i.e., M5 species or higher) is. Accordingly, in one embodiment of the present invention, osmolality of the cell culture medium is maintained at less than about 600 mOsm/Kg to reduce or control mannose content of expressed glycoproteins (e.g., about 250 mOsm/Kg to about 600 mOsm/Kg).

For mammalian cell culture, osmolality of the cell culture medium is maintained at less than about 550 mOsm/Kg, or at less than about 500 mOsm/Kg, or at less than about 450 mOsm/Kg, or at less than about 400 mOsm/Kg or at less than about 380 mOsm/Kg, or at between about 200 mOsm/Kg and about 600 mOsm/Kg or at between about 250 mOsm/Kg and about 550 mOsm/Kg, or at between about 250 mOsm/Kg and about 500 mOsm/Kg, or at between about 250 mOsm/Kg and about 450 mOsm/Kg, or at between about 250 mOsm/Kg and about 400 mOsm/Kg, or at between about 250 mOsm/Kg and about 380 mOsm/Kg, or at between about 250 mOsm/Kg and about 350 mOsm/Kg.

In order to achieve an osmolality in the desired range, the concentration of various constituents in the culture medium can be adjusted. For example, solutes which can be added to the culture medium so as to increase the osmolality thereof include proteins, peptides, amino acids, hydrolyzed animal proteins such as peptones, non-metabolized polymers, vitamins, ions, salts, sugars, metabolites, organic acids, lipids, and the like. It will be appreciated however, that the concentration(s) of other constituents in the culture medium can be modified in order to achieve a desired osmolality.

In other embodiments, osmolality can be adjusted to the aforementioned ranges by adding one or more osmoprotectants to the culture medium. Exemplary osmoprotectants are well known in the art and include, but are not limited to, betaine, glycine, L-threonine, L-proline and derivatives thereof including, but not limited to, glycine betaine, betaine aldehyde. In a particular embodiment, a cell culture medium contains betaine at a concentration of about 20 mM or greater, or at about 1 mM to about 100 mM, and more preferably at about 20 mM to about 30 mM.

Osmolality can be measured by any of the means that are well-known in the art and those described herein. For example, an osmometer such as sold by Fisher Scientific, Pittsburgh, PA under the brandname OSMETTE can be used for measuring osmolity of a cell culture medium. Alternatively, Osmette model 2007 (Precision Systems, Inc., Natick, MA) can be used.

In other embodiments of the invention, osmolality can be adjusted by modifying the concentration of one or more of salts, sugars, peptones, amino acids and ammonium in the cell culture medium.

In still other embodiments, the aforementioned parameters affecting osmolality can be combined with manipulating the temperature and duration of time which the cells are cultured to modulate (e.g., reduce) mannose-content. Accordingly, it should be understood that the various cell culturing parameters described herein can be adjusted alone or in combination to modulate the mannose-content of recombinant glycoproteins.

(i) Potassium and Sodium Concentrations

In the experiments leading up to the present invention, it was demonstrated that an increase in potassium (K+) concentration in the culture medium contributes to the high-mannose content of glycoproteins. Accordingly, in one embodiment, the invention employs a cell culture medium having a K+ concentration of about 70 mM or less (e.g., at about 10 mM to about 50 mM).

As discussed above, the potassium concentration of the cell culture medium alone may be controlled or it may be controlled in combination with one or more of the other factors described herein which affect osmolality. In a particular embodiment, the culture medium further includes a sodium concentration of about 200 mM or less (e.g., at about 50 mM to about 100 mM).

(ii) Amino Acids

Other factors which were discovered to affect osmolality of the cell culture medium and/or contribute to high-mannose content of recombinantly expressed proteins are the concentration and type of amino acids in the medium. For example, in a particular embodiment, a doubling of the concentration of all 20 amino acids in the medium results in an increase in mannose-content. Accordingly, in a particular embodiment of the present invention, the cell culture medium is adjusted to have a reduced amino acid concentration. In a particular medium, the amino acid concentration is reduced by about half.

In another particular embodiment, the cell culture medium is substantially free of one or more amino acids selected from the group consisting of alanine, arginine, aspartic acid and glutamic acid.

(iii) Sugars

Other factors which were discovered to affect osmolality of the cell culture medium and/or contribute to high-mannose content of recombinantly expressed proteins are the concentration and type of sugars in the medium. In a particular embodiment, the cell culture medium includes glucose at a concentration of about 1 mM to about 90 mM.

(iv) Ammonium

Another factor which can affect osmolality of the cell culture medium and/or contribute to high-mannose content of recombinantly expressed proteins is the ammonium concentration of about 30 mM or less (e.g., at about 0 mM to about 10 mM). In one embodiment, the ammonium concentration is about 10 mM or less.

(v) Peptones

Other factors which were discovered to affect osmolality of the cell culture medium and/or contribute to high-mannose content of recombinantly expressed proteins are the concentration and type of peptones used in the medium. Peptones are media supplements that are produced from hydrolyzed animal proteins. Sources of peptones are well known in the art and include, for example, animal by-products, gelatins and plant materials. Exemplary peptones include, but are not limited to, yeast extract, yeast hydrolysate, soy peptone, soy hydrolysate, wheat peptone, and wheat hydrolysate, at a concentration of about 0.5 g/L to about 60 g/L.

(vi) Vitamins

Other factors which were discovered to affect osmolality of the cell culture medium and/or contribute to high-mannose content of recombinantly expressed proteins are the concentration and type of vitamins used in the medium. In a particular embodiment, the cell culture medium includes one or more vitamins selected from the group consisting of biotin, D-calcium, pantothenate, choline chloride, folic acids, i-inositol, niacinamide, pyridoxal HCl, pyridoxine HCl, riboflavin, thiamine HCl, cyanocobalamin at a concentration of about 0.00005 g/L to about 0.9 g/L.

(b) Temperature

Another factor which was discovered to contribute to high-mannose content of recombinantly expressed proteins is the temperature at which the cell culture is maintained. Accordingly, in another embodiment of the present invention, the temperature at which the host-cells are cultured is also adjusted alone or in combination with the foregoing factors (e.g., adjustment of cell culture timing and factors affecting osmolality) to modulate (e.g., reduce) mannose-content of recombinantly expressed glycoproteins. In certain embodiments, host-cells are cultured at about 31° C., or at about 32° C., or at about 33° C., or at about 34° C., or at about 35° C., or at about 36° C., or at about 37° C. or at about 38° C.

III. Cell Culture Procedures

In accordance with the methods of the present invention, host-cells are cultured in a medium that allows for the expression of recombinant glycoproteins having low-mannose content. Suitable cell culture procedures and conditions are well known in the art. Host-cells (e.g., CHO and NSO cells) may be cultured in a wide variety of formats and culture vessels. For example, host-cells may be cultured in formats designed for large scale or small scale production of glycoproteins. Additionally, host-cells may be cultured adherent to the bottom of culture flasks or dishes, or they may be in suspension in stirred flasks, bioreactors or in roller bottle cultures. In certain embodiments, for production of recombinant glycoproteins in commercially relevant quantities, host-cells may be grown in bioreactors, and preferably bioreactors having a capacity of about 2 liters or more, or about 5 liters or more, or about 10 liters or more, or about 50 liters or more, or about 100 liters or more, or about 500 liters or more, or about 1000 liters or more, or about 1500 liters or more, or about 2000 liters or more.

In certain embodiments, host-cells can be cultured (e.g., maintained and/or grown) in liquid media and preferably are cultured, either continuously or intermittently, by conventional culturing methods such as standing culture, test tube culture, shaking culture (e.g., rotary shaking culture, shake flask culture, etc.), aeration spinner culture, or fermentation. In certain embodiments, host-cells are cultured in shake flasks. In yet other embodiments, host-cells are cultured in a fermentor (e.g., in a fermentation process). Fermentation processes include, but are not limited to, batch, fed-batch and continuous methods of fermentation. The terms "batch process" and "batch fermentation" refer to a closed system in which the composition of media, nutrients, supplemental additives and the like is set at the beginning of the fermentation and not subject to alteration during the fermentation; however, attempts may be made to control such factors as pH and oxygen concentration to prevent excess media acidification and/or microorganism death. The terms "fed-batch process" and "fed-batch" fermentation refer to a batch fermentation with the exception that one or more substrates or supplements are added (e.g., added in increments or continuously) or the cell culture conditions are changed as the fermentation progresses. The terms "continuous process" and "continuous fermentation" refer to a system in which a defined fermentation media is added continuously to a fermentor and an equal amount of used or "conditioned" media is simultaneously removed, for example, for recovery of the desired product (e.g., recombinant glycoprotein). A variety of such processes have been developed and are well-known in the art.

In a particular embodiment, a host-cell expressing a recombinant human monoclonal antibody that binds IL-15 is grown in roller bottles, two-liter spinner-flasks or another suitable culture system.

IV. Recovery of the Glycoprotein

Following the polypeptide production phase, the recombinant glycoprotein of interest can be recovered from the culture medium using techniques which are well established in the art. The glycoprotein of interest preferably is recovered from the culture medium as a secreted polypeptide, although it also may be recovered from host cell lysates.

In certain embodiments, the culture medium or lysate is centrifuged to remove particulate cell debris. The glycoprotein thereafter is purified from contaminant soluble proteins and polypeptides using a suitable purification procedures. Exemplary purification procedures include, but are not limited to, fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; get filtration using, for example, Sephadex G-75; and protein A Sepharose columns to remove contaminants such as IgG. A protease inhibitor such as phenyl methyl sulfonyl fluoride (PMSF) also may be useful to inhibit proteolytic degradation during purification. One skilled in the art will appreciate that purification methods suitable for the recombinant glycoprotein of interest may require modification to account for changes in the character of the glycoprotein upon expression in recombinant cell culture.

In a particular embodiment of the present invention, a recombinant glycoprotein expressed using the methods of the present invention is a human monoclonal antibody or an antigen-binding fragment thereof. Generally, the antibodies are initially characterized by ELISA. For example, microtiter plates can be coated with purified antigen such as, for example, IL-15 in PBS, and then blocked with irrelevant proteins such as bovine serum albumin (BSA) diluted in PBS. Dilutions of extracts from cultured cells are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405.

To determine if the antibodies produced by the methods of the present invention bind to unique epitopes, each antibody can be biotinylated using commercially available reagents (Pierce, Rockford, IL). Biotinylated MAb binding can be detected with a streptavidin labeled probe. To determine the isotype of purified antibodies, isotype ELISAs can be performed using art recognized techniques. For example, wells of microtiter plates can be coated with 10 µg/ml of anti-human Ig overnight at 4° C. After blocking with 5% BSA, the plates are reacted with 10 µg/ml of antibodies or purified isotype controls, at ambient temperature for two hours. The wells can then be reacted with either human IgG1 or other human isotype specific conjugated probes. Plates are developed and analyzed as described above.

In a particular embodiment, a recombinant glycoprotein produced using the methods of the present invention is a human monoclonal antibody that binds IL-15 or an antigen-binding fragment thereof. To test the binding of IL-15 monoclonal antibodies to live cells expressing IL-15, flow cytometry can be used. Briefly, cell lines and/or human PBMCs expressing membrane-bound IL-15 (grown under standard growth conditions) are mixed with various concentrations of monoclonal antibodies in PBS containing 0.1% BSA and 0.01% NaN3 at 4° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-IL-15 human IgGs can be further tested for reactivity with the IL-15 antigen by Western blotting. Briefly, cell extracts from host-cells expressing IL-15 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, MO).

V. Pharmaceutical Compositions

In another aspect, the present invention provides a composition, e.g., a pharmaceutical composition, containing one or a combination of recombinant glycoproteins having low-mannose content. In a particular embodiment, the pharmaceutical composition includes at least one therapeutic protein having low-mannose content such as, for example, a therapeutic antibody or an antigen-binding fragment thereof having low-mannose content (e.g., a human monoclonal antibody that binds IL-15 or an antigen-binding fragment thereof). In another particular embodiment, a pharmaceutical composition of the present invention includes one or more recombinant glycoproteins having low mannose content, formulated together with a pharmaceutically acceptable carrier.

Pharmaceutical compositions of the invention also can be administered in combination therapy, i.e., combined with other agents. For example, the combination therapy can include a composition of the present invention with at least one or more additional therapeutic agents, such as anti-inflammatory agents, DMARDs (disease-modifying anti-rheumatic drugs), immunosuppressive agents, chemotherapeutics, and psoriasis agents. The pharmaceutical compositions of the invention can also be administered in conjunction with radiation therapy. Co-administration with other antibodies, such as CD4 specific antibodies and IL-2 specific antibodies, are also encompassed by the invention. Such combinations with CD4 specific antibodies or IL-2 specific antibodies are considered particularly useful for treating autoimmune diseases and transplant rejections.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the recombinant glycoprotein, e.g., an antibody, bispecific and multispecific molecule, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al., J. Pharm. Sci. 66:1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7:27 (1984)).

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the human antibodies of the invention may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations of the present invention include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.001 percent to about ninety percent of active ingredient, preferably from about 0.005 percent to about 70 percent, most preferably from about 0.01 percent to about 30 percent.

Formulations of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the therapeutic glycoproteins of the present invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see. e.g., V. V. Ranade *J. Clin Pharmacol.* 29:685 (1989). Exemplary targeting moieties include folate or biotin (see, e.g., U.S. Pat. No. 5,416, 016 to Low et al.); mannosides (Umezawa et al., *Biochem. Biophys. Res. Commun,* 153:1038 (1988)); antibodies (P. G. Bloeman et al. *FEBS Lett.* 357:140 (1995); M. Owais et al. *Antimicrob Agents Chemother.* 39:180 (1995)); surfactant protein A receptor (Briscoe et al *Am. J. Physiol.* 1233:134 (1995)), different species of which may comprise the formulations of the inventions, as well as components of the invented molecules; p120 (Schreier et al. *J. Biol. Chem.* 269:9090 (1994)); see also K. Keinanen; M. L. Laukkanen *FEBS Lett,* 346:123 (1994); J. J. Killion; I. J. Fidler *Immunomethods* 4:273 (1994). In one embodiment of the invention, the therapeutic compounds of the present invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

In a further embodiment, a recombinant glycoprotein of the present invention can be formulated to prevent or reduce the transport across the placenta. This can be done by methods known in the art, e.g., by PEGylation of the antibody or by use of F(ab)2' fragments. Further references can be made to "Cunningham-Rundles C, Zhuo Z, Griffith B, Keenan J. (1992) Biological activities of polyethyleneglycol immunoglobulin conjugates." Resistance to enzymatic degradation. J Immunol Methods. 152:177-190; and to Landor M. (1995) Maternal-fetal transfer of immunoglobulins, Ann Allergy Asthma Immunol 74:279-283. This is particularly relevant when the glycoprotein is an antibody used for treating or preventing recurrent spontaneous abortion.

A "therapeutically effective dosage" for rheumatoid arthritis preferably will result in an ACR20 Preliminary Definition of Improvement in the patients, more preferred in an ACR50 Preliminary Definition of Improvement and even more preferred in an ARCD70 Preliminary Definition of Improvement.

ACR20 Preliminary Definition of Improvement is defined as: ≥20% improvement in: Tender Joint Count (TCJ) and Swollen Joint Count (SWJ) and ≥20% improvement in 3 of following 5 assessments: Patient Pain Assessment (VAS), Patient Global assessment (VAS), Physician Global Assessment (VAS), Patent Self-Assessed Disability (HAQ), Acute Phase Reactant (CRP or ESR).

ACR50 and ACR70 are defined in the same way with ≥50% and ≥70% improvements, respectively. For further details see Felson et al. in American College of Rheumatology Preliminary Definition of Improvement in Rheumatoid Arthritis; Arthritis Rheumatism 38: 727-735 (1995).

The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The ability of the antibodies to treat or prevent psoriasis can also be evaluated according to methods well known in the art.

The composition must be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof, Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

Other embodiments of the present invention are described in the following Examples, which should not be construed as further limiting. The contents of Sequence Listing, figures and all references, patents and published patent applications cited throughout this application are expressly incorporated herein by reference.

EXAMPLES

In all the Examples discussed below, a fully human monoclonal antibody that binds IL-15 having a light chain variable region comprising the amino acid sequence set forth in SEQ ID NO:4 and a heavy chain variable region comprising the amino acid sequence set forth in SEQ ID NO:2 was used as an exemplary recombinant glycoprotein (referred to in the Examples as an "exemplary recombinant glycoprotein"). However, it would be clear to one of ordinary skill in the art that the mannose content of any recombinant glycoprotein can be modulated, as discussed herein.

Example 1: Osmolality Affects Mannose-Content of Recombinant Glycoproteins

In order to investigate the affect of osmolality on mannose-content of glycoproteins, mannose-content of an exemplary recombinant glycoprotein was analyzed at varying osmolarities in both shaker flask and bioreactor cultures. As demonstrated in FIG. 1, high-mannose content increased from about 14% to about 24% with the increase of medium osmolality from about 500 to about 580 mOsmo/Kg.

In a further experiment, 20 mM of an osmoprotectant, betaine, was added to the cell culture to provide further evidence regarding the relationship between osmolality and high-mannose content. The following table summarizes the results of one such experiment.

TABLE I

| Sample | % Hi-M |
| --- | --- |
| 36° C., culture medium | 19 |
| 36° C., culture medium + Betaine | 14 |
| 37° C., culture medium | 18 |
| 37° C., culture medium + Betaine | 13 |

Figure 2:
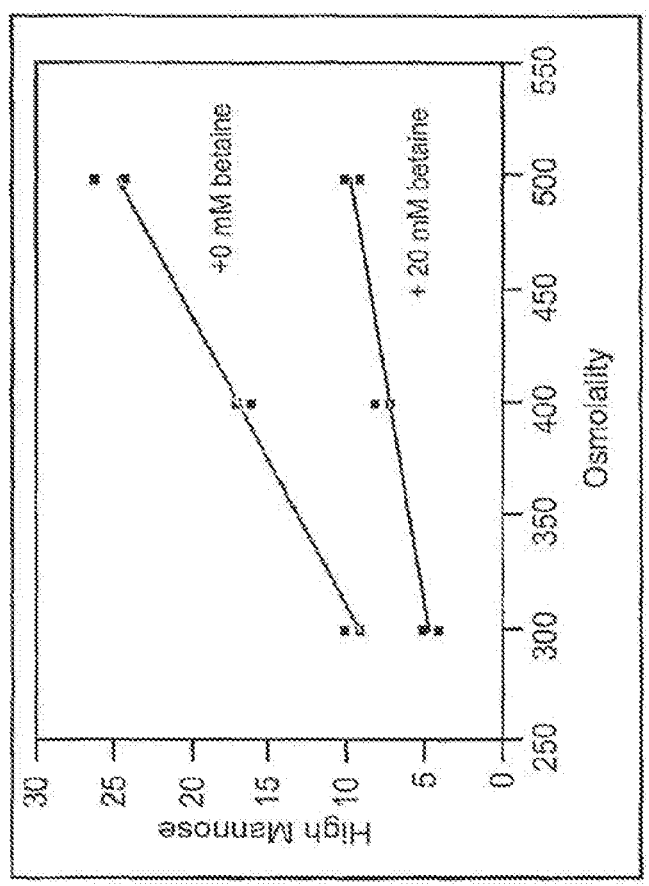
FIG. 2 is a graph depicting the correlation between addition of an osmoprotectant, betaine, and high mannose content of a fully human monoclonal antibody that binds IL-15.

Yet further evidence for the correlation between high-mannose content and osmolality is depicted in FIG. 2. Addition of about 20 mM betaine to cell culture medium dramatically reduced high-mannose content of the exemplary recombinant glycoprotein. For example, when the osmolality was about 300 mOsm/Kg, the high mannose content reduced from about 9.5% at about 0 mM betaine to about 4.5% upon the addition of 20 mM betaine (i.e., about a 5% reduction in high-mannose content). Similarly, when the osmolality was about 400 mOsm/Kg, the high mannose content reduced from about 16.5% at about 0 mM betaine to about 7.5% upon the addition of 20 mM betaine (i.e., about a 9% reduction in high-mannose content). Further, at osmolality of about 500 mOsm/Kg, the high mannose content reduced from about 25% at about 0 mM betaine to about 9.5% upon the addition of about 20 mM betaine (i.e., about 15.5% reduction in high-mannose content).

Example 2: Concentration of K+ in the Culture can be Controlled to Modulate Manose-Content of Recombinant Glycoproteins In a further experiment, the concentration of one or more salts in the cell culture medium was controlled to modulate (e.g., reduce) the mannose-content (e.g., high-mannose content) of the exemplary recombinant glycoprotein. In an exemplary experiment, the concentration of K+ in the cell culture medium was controlled and shown to affect mannose-content and specifically, the high-mannose content of the exemplary recombinant glycoprotein. Specifically, high-mannose content (i.e., M5 species or greater) of the exemplary recombinant glycoprotein produced by culturing a host-cell expressing the glycoprotein at either 15 mM or 45 mM was examined.

Figure 3:
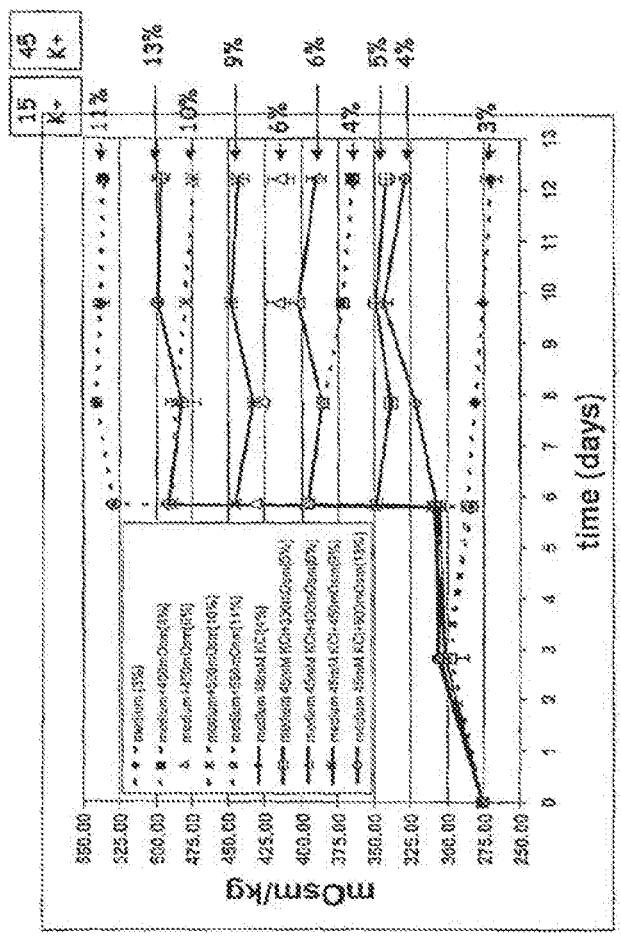
FIG. 3 is a graph depicting the correlation between osmolality and K+ concentration of culture medium.
Figure 4:
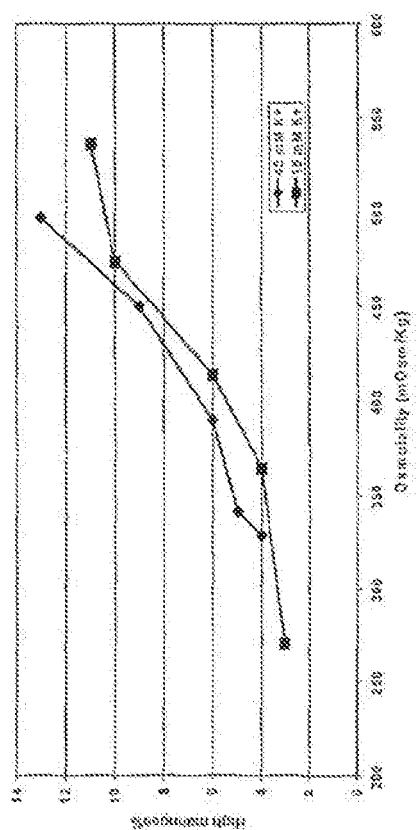
FIG. 4 is a graph depicting the correlation between high-mannose content of a fully human monoclonal antibody that binds IL-15 and osmolality, by culturing cells in a medium containing either 15 mM or 45 mM KC.

As shown in FIGS. 3 and 4, the percentage of high-mannose content increased from about 3% to about 13% with the concomitant increase in osmolality. An osmolality of between about 370 and about 500 mOsm/Kg led to an increase in high-mannose content that exceeded 10% of the glycoprotein composition.

Figure 5:
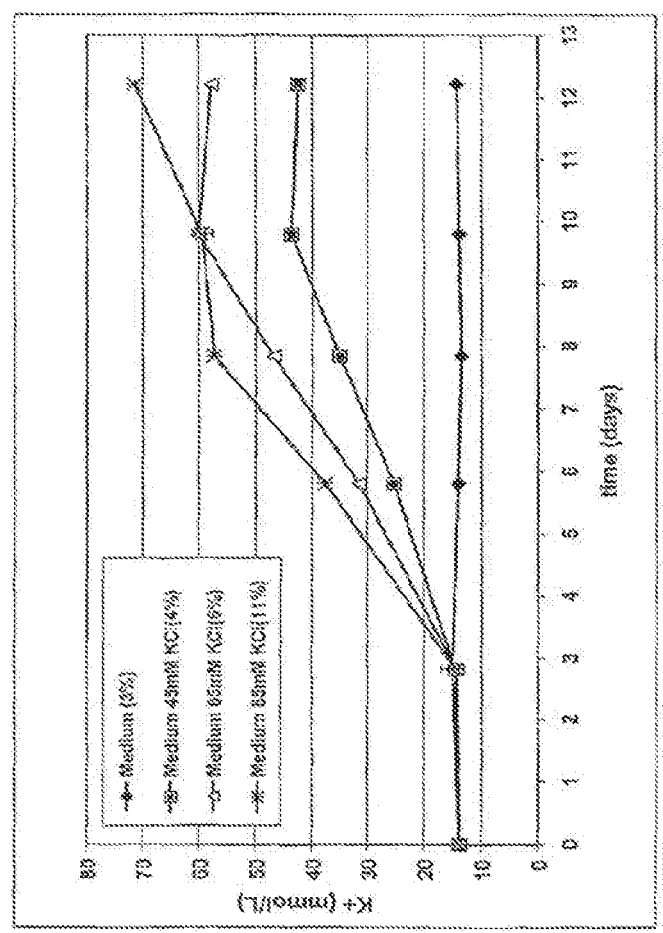
FIG. 5 is a graphical representation of the correlation between the K+ concentration and high-mannose content, showing that the optimal concentration of K+ for keeping the high-mannose content below 10% is between about 0 and about 70 mM.

In a further experiment, it was demonstrated, as shown in FIG. 5, that optimum concentration range for K+ concentration in the cell culture medium is about 0 mM to about 70 mM in order to keep the percentage of high-mannose content of a recombinant glycoprotein below 10%.

Example 3: Concentration of Na+ in the Cell Culture Medium can be Controlled to Modulate Mannose-Content of Recombinant Glycoproteins In a further experiment, the concentration of Na+ was controlled to modulate (e.g., reduce) high-mannose content of the exemplary recombinant glycoprotein. In an exemplary experiment, an increase in Na+ concentration in the cell culture medium was shown to contribute to an increase in the percentage of the high-mannose content of the exemplary recombinant glycoprotein.

Figure 6:
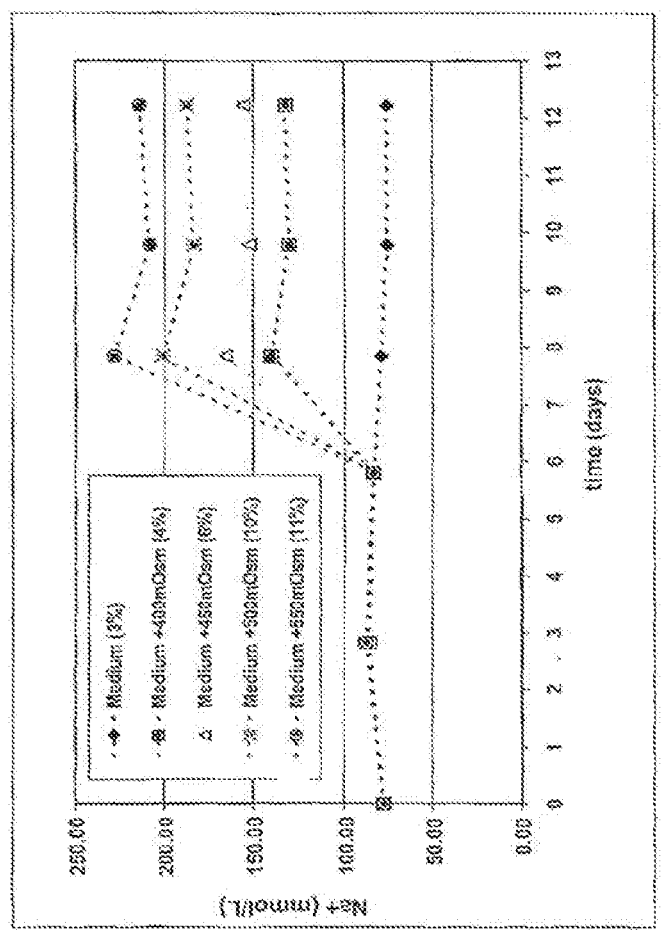
FIG. 6 is a graph representing the correlation between Na+ concentration and high-mannose content, showing that the optimal concentration of Na+ for keeping the high-mannose content below 10% is between about 0 mM and about 200 mM.

FIG. 6 demonstrates that the optimum concentration range for Na+ is between about 0 mM and about 200 mM in order to keep the percentage of the high-mannose content below 10%.

Figure 7:
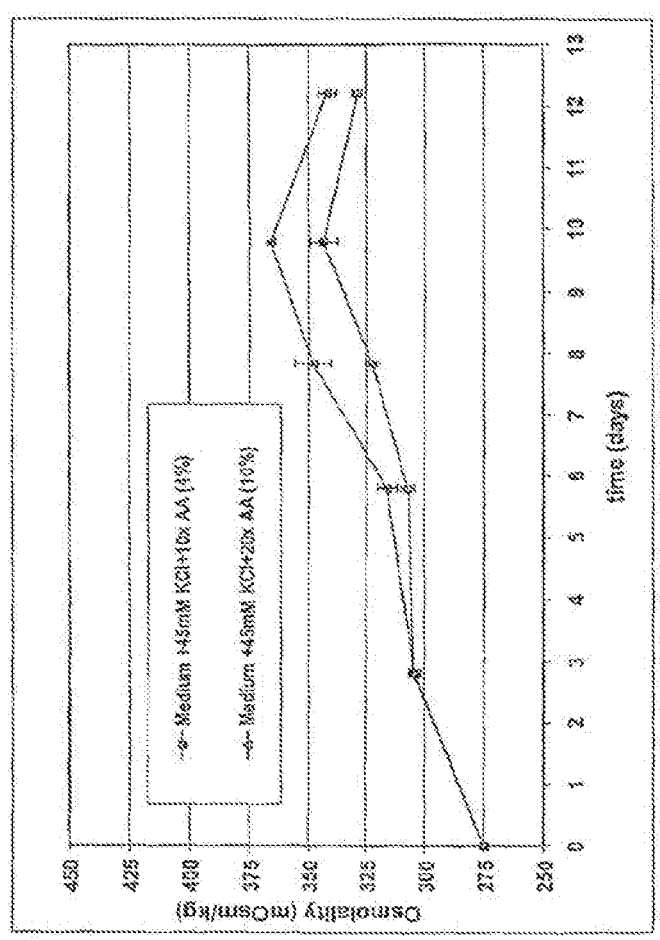
FIG. 7 is a graph depicting the correlation between amino acid concentration and high-mannose content.

Example 4: Amino Acids Contribute to High-Mannose Content of Recombinant Glycoproteins In another experiment, the effect of amino acids present in a cell culture medium was examined on the high-mannose content of the exemplary recombinant glycoprotein. As shown in FIG. 7, the percentage of high-mannose content of a recombinant glycoprotein increases from about 4% to about 10% by doubling the concentration of 20 amino acids in the feed medium. This experiment demonstrated that a medium enriched for amino-acids results in an increase in the content of high-mannose glycoproteins expressed by a host-cell cultured in such medium.

Figure 8:
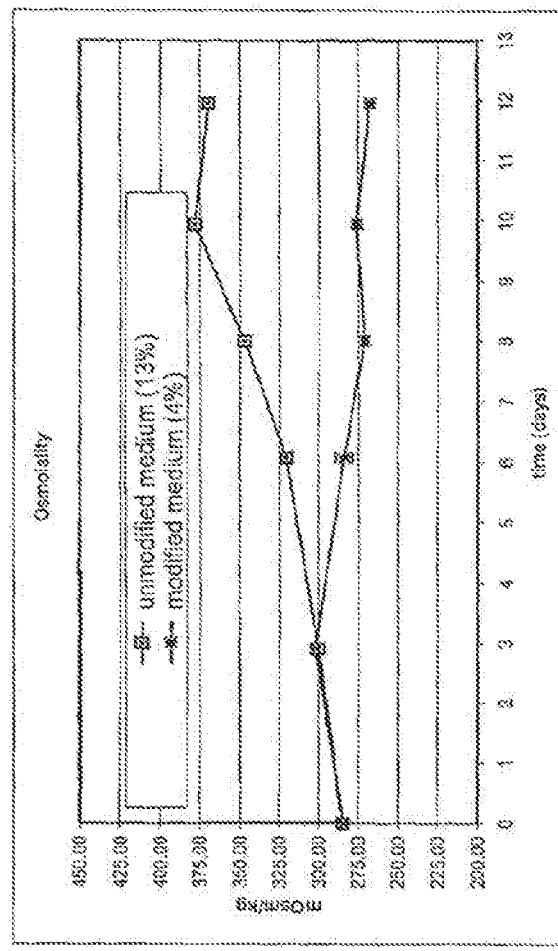
FIG. 8 is a graph depicting the correlation between the type of feed medium used and high-mannose content.

Example 5: Overall Composition of the Feed Medium Composition can Contribute to High-Mannose Content of Recombinant Glycoproteins In this experiment, the effect of different types of feed media was examined on the high-mannose content of an exemplary recombinant glycoprotein. Specifically, the effect of a modified feed medium substantially-free of the amino acids L-Alanine, L-Arginine HCL, L-Aspartic Acid and L-Glutamic Acid, and also having a lower concentration of CaCl, MgCl, KCl and sodium pyruvate relative to unmodified medium was investigated on the high-mannose content of the exemplary recombinant glycoprotein. As depicted in FIG. 8, the high-mannose content was about 4% when the modified feed medium was used and this percentage increased to about 13% when the unmodified feed medium was used.

Example 6: Effect of Temperature on High-Mannose Content

The effect of four different temperatures on high-mannose content was examined using two different feed media. The following data in Table II indicates that there was an increase in the percentage of high-mannose content with an increase in temperature.

TABLE II

| Sample Name | 36° C. | | 35° C. | | 34° C. | |
| --- | --- | --- | --- | --- | --- | --- |
| | Conc. (g/L) | % Hi-Man | Conc. (g/L) | % Hi-Man | Conc. (g/L) | % Hi-Man |
| feed medium 1 | 3.2 | 14 | 3.1 | 17 | 2.8 | 22 |
| feed medium 2 | 2.0 | 13 | 2.1 | 13 | 2.1 | 14 |

The specification is most thoroughly understood in light of the teachings of the references cited within the specification which are hereby incorporated by reference. The embodiments within the specification provide an illustration of embodiments in this disclosure and should not be construed to limit its scope. The skilled artisan readily recognizes that many other embodiments are encompassed by this disclosure. All publications and patents cited and sequences identified by accession or database reference numbers in this disclosure are incorporated by reference in their entirety. To the extent the material incorporated by reference contradicts or is inconsistent with the present specification, the present specification will supersede any such material. The citation of any references herein is not an admission that such references are prior art to the present disclosure.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters am approximations and may very depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating celiac disease, comprising administering to a subject a composition comprising an antibody or an antigen-binding fragment thereof,
   wherein fewer than about 10% of the antibody or antigen-binding fragment molecules in the composition have more than 4 mannose residues per N-linked oligosaccharide, and
   wherein the antibody or antigen-binding fragment thereof comprises:
      a light chain variable region comprising the CDRs of the light chain variable region sequence set forth in SEQ ID NO:4, and
      a heavy chain variable region comprising the CDRs of the heavy chain variable region sequence set forth in SEQ ID NO:2.

2. The method of claim 1, wherein the composition comprises an antibody or an antigen-binding fragment thereof, wherein the antibody or an antigen-binding fragment thereof comprises:
      a light chain variable region comprising the amino acid sequence set forth in SEQ ID NO: 4, and
      a heavy chain variable region comprising the amino acid sequence set forth in SEQ ID NO:2.

3. The method of claim 1, wherein the composition comprises an antibody, wherein the antibody comprises:

a light chain variable region comprising the amino acid sequence set forth in SEQ ID NO: 4, and a heavy chain variable region comprising the amino acid sequence set forth in SEQ ID NO:2.

4. The method of claim 1, wherein the composition further comprises a pharmaceutically acceptable carrier.

5. The method of claim 2, wherein the composition further comprises a pharmaceutically acceptable carrier.

6. The method of claim 3, wherein the composition further comprises a pharmaceutically acceptable carrier.

\* \* \* \* \*

SEQUENCE LISTING

<160> NUMBER OF SEQ ID NOS: 10

<210> SEQ ID NO 1

```
<211> LENGTH: 390
<212> TYPE: DNA
<213> ORGANISM: Homo sapiens
<220> FEATURE:
<221> NAME/KEY: CDS
<222> LOCATION: (1)..(390)

<400> SEQUENCE: 1 gag gtg cag ctg gtg cag tct gga gca gag gtg aaa aag ccc ggg gag      48
Glu Val Gln Leu Val Gln Ser Gly Ala Glu Val Lys Lys Pro Gly Glu
1               5                   10                  15 tct ctg aag atc tcc tgt aag gtt tct gga tac ttc ttt acc acc tac      96
Ser Leu Lys Ile Ser Cys Lys Val Ser Gly Tyr Phe Phe Thr Thr Tyr
            20                  25                  30 tgg atc ggc tgg gtg cgc cag atg ccc ggg aaa ggc ctg gag tat atg     144
Trp Ile Gly Trp Val Arg Gln Met Pro Gly Lys Gly Leu Glu Tyr Met
        35                  40                  45 ggg atc atc tat cct ggt gac tct gat acc aga tac agc ccg tcc ttc     192
Gly Ile Ile Tyr Pro Gly Asp Ser Asp Thr Arg Tyr Ser Pro Ser Phe
    50                  55                  60 caa ggc cag gtc acc atc tca gcc gac aag tcc atc agc acc gcc tac     240
Gln Gly Gln Val Thr Ile Ser Ala Asp Lys Ser Ile Ser Thr Ala Tyr
65                  70                  75                  80 ctg cag tgg agc agc ctg aag gcc tcg gac acc gcc atg tat tac tgt     288
Leu Gln Trp Ser Ser Leu Lys Ala Ser Asp Thr Ala Met Tyr Tyr Cys
                85                  90                  95 gcg aga ggg ggt aac tgg aac tgc ttt gac tac tgg ggc cag gga acc     336
Ala Arg Gly Gly Asn Trp Asn Cys Phe Asp Tyr Trp Gly Gln Gly Thr
            100                 105                 110 ctg gtc acc gtc tcc tca gcc tcc acc aag ggc cca tcg gtc ttc ccc     384
Leu Val Thr Val Ser Ser Ala Ser Thr Lys Gly Pro Ser Val Phe Pro
        115                 120                 125 ctg gca                                                              390
Leu Ala
    130

<210> SEQ ID NO 2
<211> LENGTH: 130
<212> TYPE: PRT
<213> ORGANISM: Homo sapiens

<400> SEQUENCE: 2

Glu Val Gln Leu Val Gln Ser Gly Ala Glu Val Lys Lys Pro Gly Glu
1               5                   10                  15

Ser Leu Lys Ile Ser Cys Lys Val Ser Gly Tyr Phe Phe Thr Thr Tyr
            20                  25                  30

Trp Ile Gly Trp Val Arg Gln Met Pro Gly Lys Gly Leu Glu Tyr Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Asn Trp Asn Cys Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala
    130
```

<210> SEQ ID NO 3
<211> LENGTH: 357
<212> TYPE: DNA
<213> ORGANISM: Homo sapiens
<220> FEATURE:
<221> NAME/KEY: CDS
<222> LOCATION: (1)..(357)

<400> SEQUENCE: 3

```
gaa att gtg ttg acg cag tct cca ggc acc ctg tct ttg tct cca ggg        48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc        96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc       144
Tyr Leu Ala Trp Tyr Gln Gln Lys Pro Gly Gln Ala Pro Arg Leu Leu
        35                  40                  45 atc tat ggt gca tcc cgc agg gcc act ggc atc cca gac agg ttc agt       192
Ile Tyr Gly Ala Ser Arg Arg Ala Thr Gly Ile Pro Asp Arg Phe Ser
    50                  55                  60 ggc agt ggg tct ggg aca gac ttc act ctc acc atc agc aga ctg gag       240
Gly Ser Gly Ser Gly Thr Asp Phe Thr Leu Thr Ile Ser Arg Leu Glu
65                  70                  75                  80 cct gaa gat ttt gca gtg tat tac tgt cag cgg tat ggt agc tca cac       288
Pro Glu Asp Phe Ala Val Tyr Tyr Cys Gln Arg Tyr Gly Ser Ser His
                85                  90                  95 act ttt ggc cag ggg acc aag ctg gag atc agc cga act gtg gct gca       336
Thr Phe Gly Gln Gly Thr Lys Leu Glu Ile Ser Arg Thr Val Ala Ala
            100                 105                 110 cca tct gtc ttc atc ttc ccg                                           357
Pro Ser Val Phe Ile Phe Pro
        115
```

<210> SEQ ID NO 4
<211> LENGTH: 119
<212> TYPE: PRT
<213> ORGANISM: Homo sapiens

<400> SEQUENCE: 4

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Arg Tyr Gly Ser Ser His
                85                  90                  95

Thr Phe Gly Gln Gly Thr Lys Leu Glu Ile Ser Arg Thr Val Ala Ala
            100                 105                 110

Pro Ser Val Phe Ile Phe Pro
        115
```

<210> SEQ ID NO 5
<211> LENGTH: 5

```
<212> TYPE: PRT
<213> ORGANISM: Homo sapiens

<400> SEQUENCE: 5

Thr Tyr Trp Ile Gly
1               5

<210> SEQ ID NO 6
<211> LENGTH: 16
<212> TYPE: PRT
<213> ORGANISM: Homo sapiens

<400> SEQUENCE: 6

Ile Ile Tyr Pro Gly Asp Ser Asp Thr Arg Tyr Ser Pro Pro Phe Gln
1               5                   10                  15

<210> SEQ ID NO 7
<211> LENGTH: 8
<212> TYPE: PRT
<213> ORGANISM: Homo sapiens

<400> SEQUENCE: 7

Gly Asn Trp Asn Cys Phe Asp Tyr
1               5

<210> SEQ ID NO 8
<211> LENGTH: 12
<212> TYPE: PRT
<213> ORGANISM: Homo sapiens

<400> SEQUENCE: 8

Arg Ala Ser Gln Ser Val Ser Ser Ser Tyr Leu Ala
1               5                   10

<210> SEQ ID NO 9
<211> LENGTH: 7
<212> TYPE: PRT
<213> ORGANISM: Homo sapiens

<400> SEQUENCE: 9

Gly Ala Ser Arg Arg Ala Thr
1               5

<210> SEQ ID NO 10
<211> LENGTH: 8
<212> TYPE: PRT
<213> ORGANISM: Homo sapiens

<400> SEQUENCE: 10

Gln Arg Tyr Gly Ser Ser His Thr
1               5
```